United States Patent [19]

Hunter Jackson et al.

[11] Patent Number: 5,064,657
[45] Date of Patent: Nov. 12, 1991

[54] SPIDER TOXINS AND METHODS FOR THEIR USE AS BLOCKERS OF AMINO ACID RECEPTOR FUNCTION

[75] Inventors: J. R. Hunter Jackson; Thomas N. Parks, both of Salt Lake City, Utah

[73] Assignee: University of Utah, Salt Lake City, Utah

[21] Appl. No.: 523,608

[22] Filed: May 11, 1990

Related U.S. Application Data

[63] Continuation of Ser. No. 921,218, Oct. 20, 1986, Pat. No. 4,925,664.

[51] Int. Cl.$^5$ .............................................. C07K 15/00
[52] U.S. Cl. ..................................... 424/537; 424/538
[58] Field of Search .............................. 424/537, 538

[56] References Cited

U.S. PATENT DOCUMENTS 4,855,405  8/1989  Yoshioka ........................ 424/537 X

FOREIGN PATENT DOCUMENTS 85301459  10/1986  European Pat. Off. .

OTHER PUBLICATIONS

Abe, T. et al., "Effects of a Spider Toxin on the Glutaminergic Synapse of Lobster Muscle", J. Physiol. (Lond.), 339:243-252, (1983).
Adams, Michael E. et al., "Isolation and Biological Activity of Synaptic Toxins from the Venom of the Funnel Web Spider, Agelenopsis Aperia".
Adams, M. E. et al., "Multiple Synaptic Antagonists from the Venom of an Orb Weaver Spider", Society for Neuroscience Abstracts, paragraph 260.2, p. 946, (1986).
Bachmann, M., "Isolation and Partial Characterization of a Toxin from the Venom of the East African Orthognath Spider Pterinochilus spec.", Toxicon, 20:547-552, (1982).
Bateman, A. et al., "Postsynaptic Block of a Glutamatergic Synapse by Low Molecular Weight Fractions of Spider Venom", 339 Brain Research, 237, (1985).
Bowers, C. W. et al., "Isolation and Partial Characterization of a New Irreversible Presynaptic Neurotoxin from Spider Venom", Society of Neuroscience, Abstracts, 12:27, (1986).
Bowers, "Identification . . . *Hololena curta*", Proc. Natl. Acad. Sci., U.S.A., vol. 84, pp. 3506-3510, May 1987, Neurobiology.
Branton, W. D. et al., "New Presynaptic Neurotoxins from Spider Venom", Society of Neuroscience, Abstracts, 12:176, (1986).
Croucher, J. J. et al., "Anticonvulsant Action of Excitatory Amino Acid Antagonists", Science, 216:899-901, (1982).
Cruz-Hofling, M. A. et al., "Effects of Phoneutria Nigriventer Spider Venom on Mouse Peripheral Nerve", Quart. J. Exp. Physiol., 70:623-640, (1985).
Duchen, L. W. et al., "The Pharmacology of Spider Venoms", In: A. T. Tu(Ed.), Insect Poisons, Allergens and Other Invertebrate Venoms, Handbook of Natural Toxins, vol. 2, N.Y., M. Dekker, pp. 483-513, (1984).
Entwistle et al., "Isolation of a Pure Toxic Polypeptide from the Venom of the Spider Phoneutria Nigriventer and its Neurophysiological Activity on an Insect Femur Preparation", Toxicon, 20:1059-1067, (1982).
Foil, L. D. et al., "Partial Characterization of Lethal and Neuroactive Components of the Brown Recluse Spider (Loxosceles Reclusa) Venom".
Geren, C. R. et al., "The Biochemistry of Spider Venoms", In: A. T. Tu(Ed.), Insect Poisons, Allergens and Other Invertebrate Venoms, Handbook of Natural Toxins, vol. 2, N.Y., M. Dekker, pp. 441-481, (1984).
Greenamyre, J. T., "The Role of Glutamate in Neurotransmission and in Neurologic Disease", Archives of Neurology, 43:1058-1063, (1986).
Jackson, H. et al., "Non-N-Methyl-D-Aspartate Receptors Mediating Synaptic Transmission in the Avian Cochlear Nucleus: Effects of Kynurenic Acid, Dipicolinic Acid and Streptomycin", 16 Neuroscience, 171, (1985).
Jackson, H. et al., "Spider Venoms Block Synaptic Transmission Mediated by Non-N-Methyl-D-Aspartate Receptors in the Avian Cochlear Nucleus", presented to the Society of Neuroscience, Oct. 21, 1985.
Jackson, Hunter et al., "Presynaptic Blockade of Transmission by a Potent Long-Lasting Toxin from *Aglenopsis aperta* Spiders", Society for Neuroscience, Abstracts, 12:730, (1986).

(List continued on next page.)

Primary Examiner—Catherine S. Kilby Scalzo
Attorney, Agent, or Firm—Workman, Nydegger & Jensen

[57] ABSTRACT

Methods and compositions for blocking various channels and receptors within an organism are provided. For example, a toxin was isolated from the *Argiope aurantia* spider. This toxin was found to have a reversible effect on excitatory amino acid receptors. Another toxin having a molecular weight of from approximately 5,000 to approximately 7,000 daltons was isolated from the *Hololena curta* spider. This toxin was found to have an irreversible effect on excitatory amino acid receptors.

The present invention further relates to methods of treating heart and neurological diseases by applying the toxins isolated and identified. In particular, the low molecular weight toxin from *Agelenopsis aperta* may provide a treatment of certain heart conditions such as arrhythmia, angina, hypertension, and congestive heart failure. In addition, the toxins may provide beneficial effects on certain neuological conditions including seizures. It is also found that the toxins having an irreversible effect are effective as tags in probing the various components within the calcium channels and excitatory amino acid receptors and are effective insecticides and anthelmintics.

21 Claims, No Drawings

OTHER PUBLICATIONS

Jackson, Hunter et al., "Effects of Spider Venoms on Transmission Mediated by Non-N-Methyl-D-Aspartate Receptors in the Avian Cochlear Nucleus", In: T. P. Hicks et al., Excitatory Amino Acid Transmission, N.Y., A. R. Liss, pp. 51-54, (1987).

Kawai, Nobufumi et al., "Spider Venom Contains Specific Receptor Blocker of Glutaminergic Synapses", 247 Brain Research, 169, (1982).

Kawai, Nobufumi et al., "Effect of a Spider Toxin on Glutaminergic Synapses in the Mammalian Brain", 3 Biomedical Research, 353, (1982).

Kawai, Nobufumi et al., "Block of Glutamate Receptors by a Spider Toxin", (1983).

Kawai, Nobufumi et al., "Blockage of Synaptic Transmission in the Squid Giant Synapse by a Spider Toxin (JSTX)", 278 Brain Research, 346, (1983).

Kawai, Nobufumi et al., "Spider Toxin (JSTX) on the Glutamate Synapse", 79 J. Physiol., Paris, 228, (1984).

Love, S. et al., "Morphological Abnormalities in Myelinated Nerve Fibers Caused by Leiurus, Centruoides and Phoneutria Venoms and Their Prevention by Tetrodotoxin", Quart. J. Exp. Physiol., 71:115-122, (1985).

Meldrum, B., "Excitatory Amino Acids and Anoxic/Ischaemic Brain Damage", Trends Neuroscience, 8:47-48, (1985).

Michaelis, E. K. et al., "Spider Venoms Inhibit L--Glutamate Binding to Brain Synaptic Membrane Receptors", 81 Proc. Natl. Acad. Sci. USA, 5571, (Sep. 1984).

Miller, R. J. "Toxin Probes for Voltage Sensitive Calcium Channels", Trends in Neuroscience, 7:309, (1984).

Miller, R. J., "Multiple Calcium Channels and Neuronal Function", Science, 235:46-52, (1987).

Nagai, Takatoshi et al., "Differential Blocking Effects of a Spider Toxin on Synaptic and Glutamate Responses in the Afferent Synapse of the Acoustico-lateralis Receptors of Plotosus", 300 Brain Research, 183, (1984).

Nemeth, E. F. et al., "Pharmacological Evidence for Synaptic Transmission Mediated by Non-N-Methyl-D-Aspartate Receptors in the Avian Cochlear Nucleus", 40 Neuroscience Letters, 39, (1983).

Nemeth, E. F. et al., "Evidence for the Involvement of Kainate Receptors in Synaptic Transmission in the Avian Cochlear Nucleus", 59 Neuroscience Letters, 297, (1985).

Odell, G. V. et al., "A Review of Research on Tarantula Colony Maintenance, Venom Collection, Composition and Toxicity".

Quicke, Donald L. J. et al., "Postsynaptic Blockage of Locust Neuromuscular Transmission by Low Molecular Weight Fractions of Araneid Venoms".

Rees, Riley et al., "Clinical Treatment of Confirmed Brown Recluse Spider Bites with Dapsone and Antivenom".

Rothman, S. M. et al., "Glutamate and the Pathophysiology of Hypoxic-Ischemic Brain Damage", Annals of Neurology, 19:105-111, (1986).

Saito, Mitsuyoshi et al., "Spider Toxin (JSTX) Blocks Glutamate Synapse in Hippocampal Pyramidal Neurons", 346 Brain Research, 397, (1985).

Schwarcz et al., "Excitatory Amino Acid Antagonists Provide a Therapeutic Approach to Neurologic Disorders", The Lancet, Jul. 20, 140-143, (1985).

Sheumack et al., "A Comparative Study of Properties and Toxic Components of Funnel Web Spider (Atrax) Venom", Comp. Biochem. Physiol., 78C:55-66, (1984).

Sperelakis, N., "Properties of Calcium-Dependent Slow Action Potentials: Their Possible Role in Arrhythmias", In: L. H. Opie (Ed.), Calcium Antagonists and Cardiovascular Disease, N.Y., Raven Press, pp. 277-291, (1984).

Sperelakis, N. et al., "Properties of Myocardial Calcium Slow Channels and Mechanism of Action of Calcium Antagonistic Drugs, Current Topics in Membrane and Transport", 25:44-76, (1985).

Tashumukhamedov, B. A. et al., "Effects of Different Spider Venoms on Artificial and Biological Membranes", Toxins as Tools in Neurochemistry, (1983).

Tashumukhamedov, B. A., "Reconstitution in Bilayer Lipid Membranes of the Crab Potamon Transcaspicum Spider Venom Sensitive Glutamate Receptors", 4 Gen. Physiol. Biophys., 625, (1985).

Tzeng, Mu-Chin et al., "Chemistry and Actions of a-Latrotoxin from Black Widow Spider Venom".

Usherwood, Peter N. R. et al., "Slowly-Reversible Block of Glutamate Receptor-Channels by Venoms of the Spiders, Argiope trifasciata and Araneus Gemma", 79 J. Physiol., Paris, 241, (1984).

Usherwood, Peter N. R. et al., "Antagonism of Glutamate Receptor Channels Complexes by Spider Venom Polypeptides", 6 NeuroToxicology, 239, (1985).

Usmanov, P. B. et al., "Study of the Effect of Lityphantes Payukullianus Spider Venom on Synaptic Processes", Biol. Nauki (Moscow), 9:23-28, (1982).

Usmanov, P. B. et al., "Action of Venom of the Spider Argiope lobato on the Glutamatergic and Cholinergic Synapses", (1984).

Volkova, T. M. et al., "Structural Characteristic of Argiopine-Blocker of Glutamate Channels from the Venom of Spider Argiope Lobata", presented at the Sixth European Society for Neurochemistry General Meeting in Prague, (1986).

Vyklicky, Ladislav, Jr. et al., "Spider Venom of Araneus Opens and Desensitizes Glutamate Channels in Chick Spinal Cord Neurones", 68 Neuroscience Leters, pp. 227-231, (1986).

Vyklicky, L., Jr. et al., "Araneus Spider Venom Opens and Desensitizes Glutamate in Chick Spinal Cord Neurones", presented at the Sixth European Society for Neurochemistry General Meeting in Prague, (1986).

Watkins, J. C., "Excitatory Amino Acids and Central Synaptic Transmission", Trends in Pharmacological Sciences, Sep., (1984).

Young, E. F. et al., "Neurotoxic Action of the Venom of the Common American House Spider", Physiol. Zool., 57:521-529, (1984).

SPIDER TOXINS AND METHODS FOR THEIR USE AS BLOCKERS OF AMINO ACID RECEPTOR FUNCTION

This application is a continuation of application Ser. No. 06/921,218, filed Oct. 20, 1986, now U.S. Pat. No. 4,925,664.

BACKGROUND

1. The Field of the Invention

The present invention generally relates to the isolation of certain toxins from spider venoms and the use of those toxins as inhibitors of the functions of ion channels and neurotransmitter receptors. In particular, the present invention relates to spider venom toxins and their use as blockers of calcium channels and excitatory amino acid receptors in the cardiovascular, central nervous, and neuromuscular systems of organisms, including humans.

2. The Background of the Invention

Movement of calcium ions across cell membranes is a critically important event in the normal functioning of excitable tissues such as vascular smooth muscle, cardiac muscle, and the central nervous system. Influx of calcium ions through specialized channels in the cell membranes regulates release of substances such as hormones and neurotransmitters.

The movement of calcium ions also regulates contraction of heart muscle and of vascular smooth muscle in the wall of blood vessels. Abnormal influx of calcium ions has been reported to play a role in the pathogenesis of various cardiovascular disorders (e.g., anoxic/ischemic heart disease), and drugs capable of blocking the movement of calcium through calcium channels have been used for treatment of cardiac arrhythmias, coronary artery disease, and cardiomyopathy.

The currently used drugs, however, have non-specific physiological effects and varying tissue specificities that can lead to undesirable side-effects in patients. Moreover, there are several known subtypes of calcium channel with varying physiological action and no drug that specifically blocks certain of these subtypes is known.

In the nervous system, calcium influx into the presynaptic nerve terminal via calcium channels is a necessary prerequisite for the release of chemical neurotransmitter at synapses and thus for the proper functioning of these synapses. Lowering of the extracellular calcium concentration is routinely used by neurophysiologists to reduce or abolish synaptic transmission in isolated pieces of nervous tissue.

It has not been possible, however, to specifically affect synaptic transmission in vivo in the central nervous system ("CNS") by manipulating the function of neuronal calcium channels. With the exception of the omega-conotoxin recently isolated from the venom of the marine snail *Conus geographus*, no drug with sufficiently specific or potent effects on CNS calcium channels is known.

Abnormal influx of calcium is thought to be very important in the pathogenesis of several CNS disorders, including anoxic/ischemic (stroke) damage, epilepsy, and the neuronal death associated with chronic epilepsy. Again, the paucity of chemical agents that potently and specifically block CNS calcium channels has prevented the development of an effective drug therapy for these prevalent neurological problems.

In addition, excitatory amino acids ("EAA"), most notably glutamate and aspartate, are the predominant excitatory neurotransmitter in the vertebrate (including human) CNS. As such, they play a fundamental role in the many functions of the normal nervous system. EAA's are released from presynaptic nerve terminals and, after diffusing across the synaptic cleft, contact special EAA receptor molecules in the postsynaptic cell membrane. These receptors indirectly influence the flow of various ions across the cell membrane and thus contribute to production of an electrical response to the chemical message delivered by EAA neurotransmitter molecules. A number of common and very serious neurological problems involve abnormal function of EAA synapses. These include epilepsy, several degenerative disorders such as Huntington's disease, and neuronal death following stroke.

Unfortunately, there are very few chemical agents which are potent and selective blockers (that is "antagonists") of EAA receptors. This has severely hampered research on the normal function of EAA's and limited therapeutic approaches to disorders involving EAA's.

One notable limitation of the currently available EAA receptor antagonists is the lack of any drugs with very high affinity for the receptor. A drug with high affinity for the receptor could be expected to produce irreversible blockade of synaptic transmission. When labeled with some tracer molecule, such a drug would provide a reliable way of tagging receptors to permit measurement of their number and distribution within cells and tissues. These features would have very valuable consequences for research on EAA neurotransmission and for the development of therapeutic agents to treat EAA dysfunction in humans and animals.

Arthropod animals, including insects, and certain parasitic worms use EAA's as a major chemical neurotransmitter at their neuromuscular junction and in their CNS. Because of the damage done by insect pests and the prevalence of parasitic worm infections in animals and humans in many countries, there is a constant need for potent and specific new pesticides and anthelmintic drugs that are non-toxic to humans, pets, and farm animals.

As described above, it would be a very considerable improvement in the art if it were possible to develop chemical agents that specifically and potently block calcium channel function in the CNS, cardiac muscle, and vascular smooth muscle. In particular, it would be an advancement in the art to provide a specific blocker for specific subtypes of calcium channel. Similarly, it would be an advancement in the art to provide a specific blocker of calcium channels in the CNS.

It would be a further significant advancement in the art if chemical compositions could be found that specifically bind to and block the function of EAA in the CNS of vertebrates (including humans) and in the nervous systems of invertebrates. It would be a further advancement in the art to provide calcium channel blockers and EAA receptor blockers whose actions were selectively reversible or irreversible for use in clinical settings or as research tools. It would be an additional advancement in the art to provide calcium channel blockers and EAA receptor blockers that were acceptable for use as insecticides and anthelmintics.

Such chemical compositions and methods for their use are disclosed and claimed below.

BRIEF SUMMARY AND OBJECTS OF THE INVENTION

The present invention is related to the isolation, identification, and use of various spider venoms and toxins contained within these venoms. In particular, the present invention is related to the isolation and use as calcium channel blockers or excitatory amino acid receptor blockers of certain toxins from spider venom.

As discussed above, calcium channels are intimately involved in the functions of the cardiovascular system since calcium influx affects contraction of cardiac muscle and vascular smooth muscle. Similarly, calcium influx into nerve cells is required for the release of chemical neurotransmitter substances at synapses and, therefore, for the normal functioning of the nervous system. Abnormal calcium influx into cells is associated with serious cardiovascular and neurological disorders.

As also discussed above, EAA receptors mediate synaptic transmission at the most common excitatory chemical synapse in vertebrate brain and, therefore, play a profound role in normal functioning of the nervous system. Dysfunction of EAA neurotransmission is associated with a variety of serious neurological disorders. The present invention is related to obtaining toxins from spider venoms, which toxins have specific and potent blocking effects on calcium channels or on EAA receptor within the organism.

Within the scope of the present invention, spider venom is obtained by milking spiders of various species. That is, the spider venom is obtained by electrical stimulation of the spider to cause release of the venom and subsequent suction in order to collect the released venom. This assures that impurities, which have traditionally been contained within spider venoms obtained by conventional techniques, are eliminated.

Spider venoms are known to be a complex mixture of enzymes, peptide toxins, nucleotides, free amino acids, and other molecules. As a result, in order to obtain useful spider toxins it is necessary to separate the various components of the whole spider venom. According to one embodiment of the present invention, whole venoms are fractionated by gel filtration to separate components of the venom by relative molecular mass. It will be appreciated, however, that any type of fractionation technique or other technique may be useful to obtain the spider venom toxins necessary for use in the present invention.

A group of specific spider venoms have been isolated and used extensively in the context of the present invention. The spiders that have been used within the scope of the present invention include *Agelenopsis aperta, Argiope aurantia,* and *Hololena curta.* Agelenopsis and Hololena are members of the funnel-web grass spider family Agelenidae and are commonly found in meadows and other grassy areas within the western United States.

Four specific toxins that fall within the scope of the present invention have been isolated from the Agelenopsis, Argiope, and Hololena spiders. In particular, a first high molecular weight toxin has been isolated from the *Agelenopsis aperta* spider. For ease of identification this toxin will be sometimes generally referred to as "AG1" during the present description of the invention.

It has been found that AG1 produces "irreversible" blockade of synaptic transmission under certain conditions without affecting axonal conduction of action potentials. The AG1 toxin affects transmission of the nerve impulse across the synapse. For the purpose of the present discussion, irreversible blockade is defined as blockade that is not reversed during the useful life of the various cell and tissue preparations used in experimentation with the various toxins.

AG1 is also found to irreversibly block transmission in certain central nervous system cells by blocking the transient calcium current. It is particularly noteworthy that AG1 is not acutely toxic to the cells tested and does not affect the electric excitability of the neurons themselves. Thus, suggests that AG1's effects are not produced by acute cytotoxic action. Simply stated, CNS transmission is blocked without damaging the cells involved.

A second toxin which falls within the scope of the present invention is a low molecular weight toxin also isolated from the *Agelenopsis aperta* spider, designated AG2 for purposes of this discussion. This toxin has a molecular weight of between 200 and 1,000 daltons. In particular, it is presently believed that the toxin has a molecular weight of approximately 600 daltons.

AG2 has been found to "reversibly" block synaptic transmission and its effects are diminished by increasing calcium concentrations. In experiments on cardiac muscle this toxin has also been shown to block the slow inward calcium current. Furthermore, small quantities of this toxin injected intravenously into rats significantly reduce the severity and duration of seizures induced by intravenously injected kainic acid. As a result, it can be seen that this toxin affects both the CNS and the cardiovascular system.

A further toxin within the scope of the present invention is a low molecular weight toxin isolated from the *Argiope aurantia* spider. For the purpose of this discussion this toxin is sometimes referred to as ARI. ARI has been found to be an EAA receptor blocker. This toxin produces reversible blockade of transmission of central nervous system cells.

A fourth toxin within the scope of the present invention has been isolated from the *Hololena curta* spider and has a molecular weight between 5,000 and 7,000 daltons. This toxin is sometimes designated HOI for the purpose of this discussion. HOI has been found to irreversibly and potently block CNS excitatory amino acid receptor channels without acute cytotoxicity. It will be appreciated that such a toxin is particularly adaptable for use in a research setting. Since the toxin's effect is irreversible it can be used as a tag to identify particular chemical species within cells, tissues, or organs.

The toxins discussed herein are potent and effective calcium channel or EAA receptor blockers when compared to conventional blockers. A variety of excitatory amino acid agonists and antagonists have been tested in the art for their ability to suppress synaptic transmission in the chick cochlear nucleus.

The most potent conventional antagonists, which are chemical analogs of acidic amino acids, require concentrations in the millimolar range to completely suppress the transmission. Even then, the effect of these drugs is complete reversed within 20 minutes. In contrast, partially purified spider toxins within the scope of the present invention can irreversibly block transmission with concentrations conservatively estimated to be less than one micromolar.

As a result, it will be appreciated that the present invention provides the capability to block, either reversibly or irreversibly, specific calcium channels or EAA receptors. For example, calcium channels within the cardiovascular system may be blocked with specificity. Likewise, central nervous system calcium channels may also be blocked with specificity. In the alternative, when applying AG1 toxin, both central nervous system and cardiac systems may be blocked using the same toxin.

It will also be appreciated that the present invention provides the ability to effectively block specific channels using a very small concentration of toxin. The effectiveness of the present invention is at least one order of magnitude higher than the most potent currently known blocker of EAA transmission.

As discussed above, many uses for specific channel blockers are known and many other uses are possible. For example, a channel blocker which impacts the cardiovascular system may be an effective treatment for high blood pressure. Such a channel blocker may also have usefulness in treating arrhythmia, angina, and other types of heart disease.

As a further matter, such channel blockers may be effective treatments of post cardiac arrest cell damage. It is known in the art that cell damage to the heart following a heart attack is to a significant degree due to increases in intracellular calcium concentration. As a result, a calcium channel blocker may help prevent cell damage that would otherwise occur.

Similarly, specific channel blockers with activity on the central nervous system may have the potential to treat various neurological diseases. It has been found, for example, that these channel blockers may act as a treatment of epilepsy. In addition, channel blockers of the type disclosed in the present invention may also be used in treatments of degenerative central nervous system diseases such as Alzheimer's disease.

As a related matter, it will be appreciated that EAA receptor blockers and calcium blockers of the type disclosed herein may be used as insecticides and anthelmintics because the molecules disclosed within the present invention can be applied to insects with great effectiveness for eliminating those insects and related pests.

As a result, it is a primary object of the present invention to provide EAA receptor blockers and calcium channel blockers and methods for their use which have specific and identifiable effects on an organism.

It is a further object of the present invention to provide specific calcium receptor blockers.

Similarly, it is an object of the present invention to provide specific excitatory amino acid receptor blockers.

Another object of the present invention is to provide a specific calcium channel blocker which affects only the central nervous system.

Additionally, it is an object of the present invention to provide calcium channel blockers which have effects on the cardiovascular system.

It is another object of the present invention to provide calcium channel blockers and EAA receptor blockers which are selectively reversible or irreversible in their effects for use as research tools and for use in the clinical setting.

Finally, it is an object of the present invention to provide calcium channel blockers and EAA receptor blockers which are usable as insecticides and anthelmintics.

These and other objects of the present invention will become apparent upon reading the following detailed description and appended claims.

DETAILED DESCRIPTION OF THE PREFERRED EMBODIMENTS

As discussed above, the present invention is related to new and unique calcium channel blockers and EAA receptor blockers, methods for their isolation, and methods of application of such molecules. In particular, the present invention relates to the use of isolated toxins obtained from spider venom for use as specific calcium channel or EAA receptor blockers.

It has been found within the scope of the present invention that certain spider venoms may selectively act on the central nervous system. Likewise, certain spider toxins within the scope of the present invention selectively act on the cardiovascular system. More particularly, it has been found that spider venoms can have specific activities on calcium channels and/or excitatory amino acid receptors within the organism.

The toxins within the scope of the invention also eliminate many of the side effects encountered in prior art calcium channel blockers and EAA receptor blockers. The toxins of the present invention are not expected to significantly interact with other types of drugs because of their specific activity.

In addition, it is possible using the compositions of the present invention to choose either reversible or irreversible toxins depending on the preferred area of use. It is expected that for most clinical applications toxins with a reversible activity will be preferred. At the same time, toxins with irreversible activity may be preferred in the research setting where it is desirable to tag certain neurotransmitter receptors or ion channels.

An additional benefit of the present invention is that the isolated toxins act without significant cytotoxicity. Thus, the toxins do not block channels by destroying the cells within the systems in which they are active. Additionally, the toxins of the present invention generally act without affecting axonal conduction within the nervous system. It will be appreciated, therefore, that only the receptor or ion channel is affected by the toxins which act on the central nervous system.

As mentioned above, toxins which have been identified and used within the scope of the present invention include those isolated from the spiders *Agelenopsis aperta, Argiope aurantia,* and *Hololena curta.* As discussed briefly above, Agelenopsis and Hololena are members of the funnel-web grass spider family Agelenidae which includes approximately 1,000 species worldwide. These spiders are commonly found in meadows and other grassy areas in the western United States. These spiders are rather inconspicuous and develop flat funnel-shaped webs used to gather prey. Thus, these spiders must move rapidly to seize, bite, and immobilize their prey. Their venoms act rapidly and potently to paralyze insects.

Argiope is a member of the large family of orb-weaving spiders (Araneidae) which includes approximately 2,500 species. These are generally large and conspicuously decorated spiders that build large, symmetrical, and sticky webs capable of snaring flying insects.

I. TECHNIQUES FOR ISOLATION OF VENOMS

In order to avoid impurities within the spider venom and the isolated toxins, the spider venom which was used for the tests described below was electrically milked from the spiders using a method which employs safeguards to prevent contamination of the venom by abdominal regurgitate or hemolymph.

Once the spider venom is obtained by electrical milking techniques, it is further purified using gel filtration chromatography or other similar related techniques. In addition, it is frequently desirable for final fractionation of the spider venom to be performed by high performance liquid chromatography ("HPLC").

Thus, using the technique of electrically milking the spider coupled with gel filtration chromatography and high performance liquid chromatograhy it is possible to obtain purified and usable spider toxins. It will be appreciated, however, that other equivalent techniques may also be employed within the scope of the present invention in order to isolate the spider toxins used.

II. SPECIFIC TOXINS WITHIN THE SCOPE OF THE INVENTION

While it will be appreciated that additional toxins may also fall within the scope of the present invention, the following is a sampling of some of the toxins which have been specifically identified and which have the characteristics required for a usable calcium channel blocker or EAA receptor blocker as described above.

A. Agelenopsis aperta I (AG1)

Using the techniques described above relating to the collection of venom, a toxin has been isolated from the *Agelenopsis aperta* spider having a molecular weight of between 5,000 and 10,000, and more particularly estimated to be approximately 6,000. It has been found that AG1 blocks transmission in chick cochlear nucleus neurons in an in vitro preparation of chick brain stem. Blockade persists for the useful life of the preparation (8 to 12 hours) and is regarded as irreversible as that term is defined herein. Transmission at the synapse used in the experimental techniques is mediated by non-N-methyl-D-aspartate ("non-NMDA") excitatory amino acid receptors.

It has been found that even extremely low concentrations of AG1 produce complete blockade if applied for extended periods, suggesting that the toxin binds very tightly and essentially nonreversibly on or within the cell In experiments performed using the toxin, it has been found that the toxin is very potent in that exposure of the tissue to a 0.8 micromolar solution for even two minutes results in a complete blockade of synaptic transmission.

Complete blockade using AG1 on central nervous system cells occurs in the absence of presynaptic action potentials and the time course of action is unaffected by the rate of presynaptic stimulation. Partial blocks have been achieved by brief exposure to dilute AG1 toxin, were stable for at least one hour and were unaffected by increases or decreases in stimulation rate. Partial blockade by AG1, however, can be largely reversed by increasing the extracellular calcium concentration. Subsequent reduction in calcium concentration, however, causes the post synaptic response to decline to its previous level of partial blockade.

In the absence of toxin the same increase in calcium has no effect on the amplitude of responses. These results indicate that this toxin acts presynaptically to produce long lasting blockade of transmission. The effects are independent of stimulation frequency, suggesting that the toxin does not act primarily on synthesis or reuptake of transmitter. Calcium antagonism of the effects makes it improbable that the toxin causes massive release of transmitter.

In summary, it is found that this relatively high molecular weight toxin is antagonized by increasing calcium concentrations and produces irreversible blockade of synaptic transmission in cochlear chick nucleus without affecting the afferent volley. It is also found to irreversibly block transmission in chick spinal cord by blocking the transient calcium current. In addition, this toxin has been found not to be acutely toxic and does not affect the electrical excitability of cochlear nucleus neurons themselves, indicating that its effects are not produced by acute cytotoxic action.

B. Agelenopsis aperta II (AG2)

A second low molecular weight toxin has also been isolated and purified from *Agelenopsis aperta* toxin. This toxin, like AG1, has been purified by gel filtration, ion exchange, and HPLC. Following such purification, AG2 has been found to have a molecular weight of between 200 and 1,000, and most probably about 600 daltons.

It has been found that AG2 is an effective blocker which is active both in the cardiovascular system and the nervous system. In particular, it has been found that AG2 reversibly blocks synaptic transmission in chick cochlear nucleus, rat hippocampus, mouse diaphragm, and chick cardiac muscle. In addition, it has been found that in certain experimental settings AG2 is antagonized by increasing calcium concentrations.

In experiments performed on cardiac muscle it has been found that AG2 blocks the slow inward calcium current mentioned above. As a result, it will be appreciated that AG2 may be an effective calcium channel blocker in cardiac and vascular smooth muscle.

Additional experiments have been performed using AG2 in order to determine its neurological effects. In particular, rats were intravenously injected with kainic acid in order to artificially produce seizures. It was found in experiments where AG2 was injected into rats treated with kainic acid, that AG2 significantly reduced the severity and duration of the seizures induced. AG2 also has a significant effect on the nervous system and is an attractive potential treatment for epilepsy, degenerative diseases such as Alzheimer's disease, anoxic/ischemic brain damage (stroke) and other neurological problems.

C. Argiope aurantia I (ARI)

It has been previously shown that transmission between the avian cochlear nerve and neurons of the cochlear nucleus is mediated by non-N-methyl-D-aspartate receptors and, presumably, an excitatory amino acid transmitter. The effect on transmission in those settings has been determined using *Argiope aurantia* toxin (ARI) obtained and purified using the same general methods described above.

It has been found that when applying *Argiope aurantia* toxin to the cochlear nucleus that transmission is blocked within 15 minutes without affecting the afferent volley. Recovery of transmission occurs after 45 to 90 minutes of washout of the toxin.

Partial purification with gel filtration has shown that this particular toxin is a low molecular weight fraction of between approximately 500 and than 1,000 daltons, and likely about 660 daltons.

Experimentation using ARI toxin has indicated that there was no stimulus dependency in blockage of the avian cochlear nucleus by ARI. Increasing the frequency of stimulation from 0.3 to 20 Hz had no effect on the rate of blockage and suppression is equally complete and rapid even in the total absence of presynaptic stimulation and spontaneous activity.

In summary, ARI is a relatively low molecular weight toxin. In tests run on the toxin, it has been found that the toxin produces a readily reversible blockade of transmission in chick cochlear nucleus. As a result, the toxin is expected to provide reversible blockade in various central nervous system settings.

In addition, since ARI is an excitatory amino acid receptor blocker, it is expected to have devastating effects when applied to insects and other invertebrate animals if administered in sufficient quantities. As a result, ARI would be an effective insecticide or anthelmintic.

D. Hololena curta I (HOI)

An additional active toxin has been isolated from the *Hololena curta* spider. It is found that this toxin has a molecular weight of from about 5,000 to about 7,000 daltons. This particular toxin has been found to block postsynaptic response in chick cochlear nucleus. Furthermore, the effectiveness of HOI toxin has been found to be irreversible over the life of the tissue preparation but without acute cytotoxicity.

In experiments performed with *Hololena curta* spider venom, complete irreversible suppression of transmission was accomplished without affecting axonal conduction presynaptically. In repeated experiments, the postsynaptic field potential failed to recover even after more than five hours of washing in venom-free avian tyrode solution. As mentioned above, the active component of this venom appears to reside in a fraction of about 5,000 to 7,000 daltons and appears capable of acting at even lower concentrations than the Argiope venoms discussed above.

The effect of HOI venom on the survival of cultured chick ciliary ganglion cells and their ability to extend neurites has also been assessed. At a concentration that completely suppresses synaptic transmission in the chick cochlear nucleus, the venom did not produce increased mortality of the cultured ciliary ganglion cells or interfere with the extension of neurites. Further, action potentials could still be evoked from cochlear nucleus neurons by direct electrical stimulation after several hours of transmission blockade. These experiments indicate that HOI venom is not generally neurotoxic at the concentrations tested and that the apparent irreversibility of transmission blockade does not result from cochlear nucleus neurons being rendered electrically inexcitable.

E. Comparison with other Drugs

1. Excitatory amino acid receptor blockers

Tests have been run on a large variety of excitatory amino acid receptor antagonists and agonists for their ability to suppress synaptic transmission in the chick cochlear nucleus The most potent conventional antagonists (e.g., cis-2,3-piperidine dicarboxylic acid or -D-glutamylglycine) require concentrations in the millimolar range to completely suppress transmission. The agonist quisqualate also completely suppresses transmission only at millimolar concentrations, presumably by depolarizing the postsynaptic neurons.

In contrast, the toxin derived from *Hololena curta* (HOI) completely blocks transmission at a concentration of ten micromolar or less, making it at least one hundred times more potent than conventional excitatory amino acid receptor antagonists.

The actions of both AG1 and HO1 are much more persistent than those of currently available excitatory amino acid (EAA) receptor antagonists, which are readily reversible. In tests using slices from chick brain including the cochlear nucleus, transmission blocked by application of known antagonists recovered completely after only 15-30 minutes of washout with drug-free solution.

Tests performed with these spider toxins conducted under identical circumstances indicate that blockade produced by AG1 persists for 45-90 minutes, or three times longer. The persistence of HO1 is even more striking in that responses show absolutely no sign of recovery even after several hours of washout, indicating that this compound binds extremely tightly to the EAA receptor.

The long duration of action and the relatively tight binding are particularly important for a basic research application involving physical isolation and subsequent biochemical study of EAA receptors. The toxins could be used essentially as a hook with which to grab onto the receptor and separate it from other cellular elements, in much the same fashion as a-bungarotoxin has been used in the isolation of the acetylcholine receptor.

This type of isolation has not proved feasible with currently available compounds in large part because they simply do not bind tightly enough to serve as effective "hooks." Severe limits are placed on the understanding of EAA receptors, their mechanisms of function, properties of various subclasses, and molecular biology, by the present inability to isolate and directly study the receptor molecules themselves.

2. Calcium channel blockers

Receptor and voltage-activated calcium channels are of fundamental importance in the survival and function of virtually all cell types. Entry of calcium through such channels regulates a variety of cellular activities including contraction of cardiovascular muscle and the release of neurotransmitters from nerve cells. There are presently three major classes of organic calcium channel blockers, as opposed to inorganic blockers such as manganese or lanthanum. These organic calcium channel blockers include: phenylalkylamines such as verapamil; benzothiazepines such as diltiazem; and dihydropyridines such as nifedipine.

The currently available organic calcium channel blockers have pronounced actions on heart and vascular smooth muscle, although relative selectivity for these two types of tissues varies among these compounds. A second notable features of these agents is that, although they will bind to brain tissue, they have either no effect or a relatively minor effect on the function of neurons in the central nervous system, particularly as compared to their striking effects on heart and vascular smooth muscle.

The two toxins derived from *Agelenopsis aperta* venom, AG1 and AG2, have properties that very clearly distinguish them from the currently available calcium channel blockers. AG1 acts primarily, if not exclusively, on neuronal calcium channels as opposed to heart or vascular smooth muscle calcium channels. This tissue selectivity is opposite to that seen in the compounds mentioned above. Furthermore, its effects are essentially irreversible while those of currently available calcium channel blockers, with the exception of omega-toxin from the marine snail *Conus geographus*, are all reversible.

The second calcium channel blocker from *Agelenopsis aperta* venom, AG2, is also distinguished by its tissue selectivity or, more accurately, its relative lack of selectivity. This toxin is a very effective blocker of calcium channels in heart and, in addition, exerts an apparently equally significant action on neurons of the central nervous system. The actions of AG2, unlike those of AG1, are readily reversible.

Because of the importance of calcium and calcium channels to the function of various cell types, there are a variety of potential therapeutic applications of compounds within the scope of the present invention. Calcium influx through channels mediates contraction of heart and vascular muscle. Calcium channel blockers, therefore, tend to relax both heart and vascular muscle and damp arrhythmic cardiac activity.

Accordingly, calcium channel blockers are presently used in treatment of several cardiovascular disorders including angina, arrhythmia, hypertension, and cardiomyopathy. In addition, calcium antagonists tend to inhibit platelet aggregation and so may have application in coronary occlusion and coronary vasospasm. Calcium channel blockers have also been shown to exert an antiatherosclerotic action.

Analyses performed on AG2 indicate that it is a very effective blocker of calcium channels in heart muscle and, furthermore, that it exerts this effect with few if any additional actions. This is in clear contrast to currently available compounds which, in addition to blocking calcium channels, typically have other actions such as increasing or decreasing the flow of potassium through its channels. This specificity of the effects of AG2 suggests that it would have the desired therapeutic action on calcium channels with fewer unwanted side-effects arising from the use of currently available compounds.

Insofar as AG2 has a significant effect on calcium channels in the central nervous system, it has several applications to neurological disorders. There is mounting evidence that epileptic activity in the brain and resulting damage to neurons may involve calcium currents flowing through receptor or voltage-activated calcium channels. As a result, calcium channel blockers are expected to be effective in blocking seizures and preventing neuronal damage associated with seizures. Such a seizure effect is clearly indicated by the experiments described above using rats and AG2. Damage to neurons resulting from stroke seems to involve the excessive accumulation of calcium within neurons following hypoxia and the cytotoxic effects of calcium.

III. EXAMPLES

The following examples are given to illustrate particular compositions and methods within the scope of the present invention but they are not intended to limit the scope of the present invention.

EXAMPLE 1

A spider toxin within the scope of the present invention was isolated from the *Agelenopsis aperta* spider. Spider venom was obtained from, and species identification provided by, Spider Pharm, Inc. of Black Canyon City, Ariz. *Agelenopsis aperta* spiders were electrically milked using a method that employs safeguards to prevent contamination of venom by abdominal regurgitate or hemolymph. Venom was diluted 1 to 10 with avian Tyrode solution (140 mM NaCl, 4 mM KCl, 4 mM $NaHCO_3$, 1 mM $MgSO_4$, 3 mM $CaCl$, 1.2 mM $NaH_2PO_4$, 10 mM HEPES, 10 mM glucose) and fractionated by gel filtration using Bio-Gel P-10 and a 0.7 ×30 cm column and collected in 0.5 ml fractions. These fractions were assayed for blockade of synaptic transmission using the electrophysiological methods described below.

HPLC separation of gel filtration fractions was performed using a Vydac C-18 reverse phase column. Components were eluted from the column over a period of 60 minutes using a 0-60% linear gradient of 60% acetonitrile in 0.1% trifluoroacetic acid. Elution was monitored by absorbance detection at 214 nm. Peaks were collected manually, dried down, stored at $-20°$ C., and then reconstituted by varying concentrations with avian tyrode before use.

For gel electrophoresis, a 15 uL sample of each gel filtration fraction was mixed with 7.5 ul of 3× sample buffer (18% 1M tris-HCL, pH 6.8, 15% 2 mercaptoethanol, 30% glycerol, 7% sodium dodecyl-sulfate, 0.001% bromphenol blue) and the entire sample was loaded onto a 10% to 20% gradient polyacrylamide gel using the slab method. Electrophoresis was performed at 20 watts constant power for three hours. Gels were stained with Coomassie blue.

The toxin so isolated had a molecular weight of approximately 6,000 as estimated from SDS polyacrylamide gels. The toxin was bath-applied to cochlear nucleus neurons in an in vitro preparation of chick brain stem. Upon stimulation of the cochlear nerve innervating the cochlear nucleus, it was found that the toxin blocked transmission between the cochlear nerve afferents and the cochlear nucleus neurons.

After washout of the toxin with toxin-free Tyrode solution, blockade persisted for the useful life of the preparation (about 8 hours). Even extremely low concentrations of about 0.1 uM produced complete blockade if applied for extended periods of about one hour. The toxin also appeared to be quite potent in that exposure of the tissue to a 0.8 uM solution for even two minutes resulted in complete blockage of transmission.

The results suggest that blockade using the toxin so obtained is irreversible, or at the very least the toxin binds unusually tightly to its targets.

EXAMPLE 2

The high molecular weight *Agelenopsis aperta* toxin described in Example 1 was obtained using the same procedure as described in Example 1. Gel-filtration fractions having the effects described in Example 1 were diluted 1:150 with Tyrode and bath-applied for one minute to an in vitro preparation of the chick brain stem. This brief exposure to dilute toxin produced partial (about 50%) blockade of transmission.

These partial blocks were stable for at least one hour and were unaffected by increases or decreases in the rate of cochlear nerve stimulation over a range of 0-30 Hz. Partial blockade, however, was largely reversed by increasing extracellular calcium from 3 to 9 mM. Subsequent reduction of extracellular calcium back to 3 mM caused the postsynaptic response to revert to its previous level of partial blockade.

The result so obtained indicates that this toxin acts presynaptically to produce long-lasting blockade of transmission. The finding that the effects of this toxin are independent of stimulation frequency suggests that the toxin does not act primarily on synthesis or reuptake of transmitter The inverse relationship between extracellular calcium concentration and the blocking effects of the toxin, indicates that the toxin likely acts on calcium channels. This action could be exerted on presynaptic calcium channels necessary for the release of transmitter and/or on postsynaptic calcium channels involved in the response of the cochlear nucleus neurons to synaptic stimulation.

EXAMPLE 3

The toxin AG1 described in Examples 1 and 2 is obtained in the manner described above from *Agelenopsis aperta* spider venom.

The toxin so obtained is applied and a complete blockade of synaptic transmission is achieved as described in Example 1. EAA agonists quisqualic acid and kainic acid are then individually bath-applied to the cochlear nucleus neurons at concentrations of 5 mM and 50 uM, respectively.

Application of these agonists at such concentrations normally reduces the ability of cochlear nucleus neurons to respond to direct electrical stimulation, presumably by depolarizing them by their action on EAA receptors. When applied in the presence of AG1 toxin the same effect is seen; that is, after 10 minutes of application of either quisqualic of kainic acids in the presence of AG1 toxin the response of cochlear nucleus neurons to direct antidromic stimulation is reduced by about 75%. The degree and time-course of this effect are not significantly different from those observed when either quisqualic of kainic acid is applied in the absence of AG1 toxin.

The result so obtained indicates that this toxin does not exert its blocking effects on synaptic transmission by a direct action on EAA receptors on the postsynaptic neuron but rather by a direct action of the toxin on calcium channels as suggested in Examples 1 and 2. If it were acting directly on EAA receptors it would be expected that the toxin would also block the effects of directly applied EAA agonists, such as quisqualic or kainic acid. The obtained result runs counter to this expectation.

EXAMPLE 4

A spider toxin within the scope of the invention was isolated from the *Agelenopsis aperta* spider. Spider venom was obtained from Spider Pharm, Inc. of Black Canyon City, Ariz. *Agelenopsis aperta* spiders were electrically milked using a method that employs safeguards to prevent contamination of venom by abdominal regurgitate or hemolymph. Venom was diluted 1 to 10 with avian tyrode solution and fractionated by gel filtration using BioGel P-10 and a 0.7×30 centimeter column and collected in 0.5 mil fractions.

HPLC separation of gel filtration fractions was performed using a Vydac C-18 reverse phase column. Components were eluted from the column over a period of 60 minutes using a 0–60% linear gradient of 60% acetonitrile in 0.1% trifluoroacetic acid. Elution was monitored by absorbance detection at 214 nm. Peaks were collected manually, dried down, stored at $-20°$ C., and then reconstituted by varying concentrations with avian tyrode before use.

For gel electrophoresis, a 15 ul sample of each gel filtration fraction was mixed with 7.5 ul of 3× sample buffer (18% 1M tris-HCL, pH 6.8, 15% 2 mercaptoethanol, 30% glycerol, 7% sodium dodecyl-sulfate, 0.001% bromphenol blue) and the entire sample was loaded onto a 10% to 20% gradient polyacrylamide gel using the slab method. Electrophoresis was performed at 20 watts constant power for three hours. Gels were stained with Coomassie blue.

The toxin so isolated had a molecular weight of approximately 600 as estimated from SDS polyacrylamide gels.

Cultured single heart cells were prepared from 9 to 10 s day old embryonic chick hearts (ventricles) by standard techniques. The cells were dispersed in sterile HMEM (Hanks Minimum Essential Medium, Gibco) containing 0.1% trypsin and 1.8 nm $Ca^{2+}$. The cell digest was collected through sterile gauze, pooled, and centrifuged at 170 g for 10 minutes. Single cells were resuspended in culture medium and centrifuged again in order to wash out the trypsin.

Cells were then placed in a plastic dish for 30 minutes at 37° C. to allow the fibroplasts to attach themselves to the plastic dish. In order to eliminate the fibroblasts, the heart cells remaining in suspension were transferred to a new plastic dish leaving the attached fibroblasts. The culture medium was made of HMEM containing 5% fetal bovine serum (Gibco) and 50 IU/ml penicillin-G-potassium (Ayerst). The cultured heat cells were kept in a 5% $CO_2$, 95% $O_2$, incubator at 37° C. Cultured single heart cells were used after 1 to 2 days for whole-cell voltage clamp recordings.

In order to perform whole-cell voltage clamp recording, patch pipets were prepared by pulling capillary tubes in two steps using a vertical puller. The pipets were filled with a solution containing, in millimoles per liter: NaCl 20: KCl 130;$MgCl_2$2; EGTA 5; HEPES buffer 5; and glucose 5 (pH 7.4) for recording action potentials in with solutions containing: K-aspartate, 130; TEA, 20;$MgCl_2$, 2; EGTA, 5; ATP, 0.3; cAMP, 0.03; HEPES buffer, 5, and glucose, 5 (pH 7.4), for the study of ISI using whole-cell voltage clamp technique. The cells were superfused with extracellular solution containing (in millimoles per liter) for recording action potentials; NaCl, 130; KCl, 5.4; $CaCl_2$, 2.2; $MgCl_2$, 0.2; HEPES buffer, 5, and glucose, 5 (pH 7.4) at 22° C., and for the study of $I_{CA}$; TEA, 130; 4-aminopyridine, 5.4; $CaCl_2$, 1.8;$MgCl_2$, 1.03; HEPES buffer, 5, and glucose, 5 (pH 7.4) at 35° C. The pipet resistances ranged from 2 to 50 megaohms, and the seal resistance ranged from 20 to 10 G ohms.

A patch clamp amplifier was used for the voltage clamp experiments.

It was found that two of the gel-filtration fractions containing low-molecular weight had significant acute effects on the ventricular cell action potentials. One of these two fractions was abou twice as potent as the other in producing the effect described as follows. The resting membrane potential was $-80$ mV and superfusion with Tyrode solution containing a 1 to 10 dilution of the gel filtration fraction containing the toxin progressively decreased the action potential duration and overshoot. This effect indicates blockade of the slow inward calcium current ($I_{si}$). There was no effect on resting membrane potential or +Vmax, indicating that the toxin did not affect the inward fast sodium current.

EXAMPLE 5

In this example, the procedure outlined in Example 4 was followed.

In order to more directly assess the effect of the toxin on the calcium current, whole-cell voltage clamp was used and $I_{si}$ was recorded in the absence of Na and K ions. The most potent of the gel-filtration fractions, as described in Example 4, was applied to chick heart cells at various concentrations. A dilution of 1:150 decreased $I_{si}$ within 4 minutes and a steady state was established after 7 minutes. The effect was fully reversible upon washout. A dilution of 1:100 further decreased $I_{si}$ and that current was completely blocked after 10 minutes of exposure to a 1:10 dilution.

These results indicate a specific, reversible blockade of the slow inward calcium current in heart muscle by the AG2 toxin.

EXAMPLE 6

In this example, the procedure outlined in Example 4 was followed. The most potent gel-filtration fraction having the effects on heart described in Examples 4 was further purified using high performance liquid chromatography (HPLC) according to the procedure described in Example 4. The HPLC profile revealed seven major peaks. Each of these were collected and assayed for effects on the $I_{si}$ using voltage-clamp as described in Example 4. Only one of the HPLC peaks or fractions had any significant effect. At a 1:10 dilution, that fraction progressively decreased $I_{si}$ within 7 minutes and completely blocked it within 9 minutes. This effect was fully reversible upon washout of the toxin.

These results indicate that the toxin molecule producing the observed effect on calcium currents in heart has been highly purified from the original whole *Agelenopsis aperta* venom.

EXAMPLE 7

Low molecular weight toxin (AG2) is isolated as described in the procedure outlined in Example 4. Toxin so isolated is used to treat human patients suffering from angina pectoris of any of three types: stable angina on effort, unstable angina at rest, and variant angina due to vasospasm. Treatment with AG2 will decrease the frequency of anginal attacks and produce prolonged depression of the ST segment of the electrocardiogram which can significantly prolong exercise duration. During exercise, angina is diminished in severity or abolished and the requirement for nitroglycerine therapy is diminished or abolished. AG2 will produce these beneficial cardiovascular effects by one or more of the following actions: decreased systemic vascular resistance and arterial blood pressure; a direct negative inotropic effect, peripheral vasodilation, and a direct negative inotropic effect, peripheral vasodilation, and a direct negative chronotropic effect, all of which decrease myocardial oxygen consumption; dilation of coronary arteries, which improves myocardial blood supply; a specific effect on myocardial metabolism; conduction delay interfering with the reentrant cycle of tachycardia.

EXAMPLE 8

Toxin AG2 is isolated as described in Example 4 and administered to human patients suffering from hypertropic cardiomyopathy. Marked symptomatic relief is noted and one or more of the following specific improvements in cardiac function will be observed: the abnormal left ventricular diastolic properties are reverted; the prolonged left ventricular isovolumic relaxation time will decrease, left ventricular pressure decay will be accelerated, and the depressed left ventricular filling increases significantly. Left ventricular thinning is also improved and there is a significant decrease in left ventricular end-diastolic pressure and a downward shift in the left ventricular diastolic pressure-dimension curve without any effect on systolic function.

EXAMPLE 9

Toxin AG2 is isolated as described in Example 4 and administered to human patients suffering from systemic hypertension. Regular treatment with AG2 is found to provide symptomatic relief and effective control of this disorder by significantly decreasing arterial blood pressure through one or more of the following mechanisms: decreased peripheral arterial resistance, decreased pulmonary arterial resistance, and decreased pressor and aldosterone response to angiotensin II.

EXAMPLE 10

Toxin AG2 is isolated as described in Example 4 and administered, in combination with other drugs, to human patients suffering from congestive heart failure. Treatment with AG2 produces symptomatic relief and a significant improvement in cardiac function in these patients, as indicated by one or more of the following indices: a decrease in mean pulmonary artery, mean aortic, and left ventricular end-diastolic blood pressures, decreases in systemic and pulmonary vascular resistance, and an increase in cardiac index; increases in left ventricular ejection fraction and stroke volume; decreases in left ventricular volumes; a reduction in myocardial oxygen requirements; improvements in diastolic performance.

EXAMPLE 11

Toxin AG2 is isolated as described in Example 4 and administered to human patients suffering from pulmonary hypertension. Significant clinical improvement is obtained, as measured by relief of symptions and one or more of the following indices of cardiovascular function: decreased pulmonary vascular resistance; increases in cardiac output; and increases in right ventricular ejection fraction with decreases in right ventricular volumes.

EXAMPLE 12

AG2 is isolated as described in Example 4 and administered to human patients suffering from peripheral vascular disease (e.g., Raynaud's Disease). The frequency of disease attacks is reduced, as is the severity of the attacks when they occur.

EXAMPLE 13

AG2 is isolated as described in Example 4 and administered to human patients undergoing transluminal angioplastic surgery. By its transient regional cardioplegic effects and its production of increased coronary blood flow, AG2 preserves the ventricular myocardium from ischemia induced by the surgical procedure and thereby prolongs inflation periods, an important determinant of the success of transluminal angioplasty.

EXAMPLE 14

AG2 is isolated as described in Example 4 and administered to human patients with symptomatic atherosclerosis or patients at elevated risk of developing atherosclerosis. AG2 will decrease existing atherosclerotic stenosis of blood vessels (with ensuing symptomatic relief) and prevent or reduce development of atherosclerosis by one or more of the following actions: prevention of calcium accumulation in arterial walls, reduction in the force of contractility and endothelial damage caused by the bloodstream, decreased blood pressure, and anti-platelet aggregating effects.

EXAMPLE 15

AG2 is isolated as described in Example 4 and administered to patients suffering from cardiac arrhythmia of any of the following types: sinus tachycardia, supraventricular tachycardia, atrial fibrillation and flutter, ventricular premature contractions and ventricular tachycardia, premature atrial contractions, and chronic atrial fibrillation. Treatment with AG2 will provide symptomatic relief through one or more of the following actions slowing of the sinus rate, slowing of the reentrant cycle, suppression of extrasystoles responsible for the arrhythmia, a parasympathomimetic effect, or induction of ventricular ectopy interfering with the tachycardia cycle, decreasing the amplitude of action potentials in the upper and middle zone of the atrioventricular node and lengthening the effective refractory period of the atrioventricular node, which lead to slowing of the atrioventricular conduction time; interruption of a tachycardia reentry mechanism involving a slow response action potential qr a depressed fast response action potential or a slow-channel dependent triggered automaticity.

EXAMPLE 16

AG2 is isolated as described in Experiment 4 and administered to human patients suffering from achute myocardial ischemia or infarction. Significant symptomatic relief and protection of the myocardium from cellular damage is observed. These beneficial actions are due to AG2's vasodilation effects, negative inotropic effect and/or inhibition of calcium accumulation in the myocardium upon reperfusion.

EXAMPLE 17

AG2 toxin was isolated according to the procedure outlined in Example 4. Rats are intravenously injected with 12 mg/kg dose of the convulsant kainic acid. This is followed after five minutes with an I.V. injection of AG2 toxin in an amount equivalent to that derived from 50 ul of whole venom by the procedure outlined in Example 4. Control subjects receive only the kainic acid injection. Control subjects begin to show seizure activity after 10-15 minutes. By 30 minutes they show frequent (about one every two minutes) clonic-tonic seizures and after one hour show virtually continuous tonic-clonic seizures (status epilepticus). By three hours about 50% of control subjects have died. About 80% of control subjects die within 36 hours.

Subjects receiving the same dose of kainic acid but a subsequent injection of AG2 as described above, however, show virtually no seizure behavior until about 90 minutes after the kainic acid injection. Seizure behavior then increases over a period of about one hour, but only about 15% of these animals ever enter status epilepticus and none die even after 48 hours.

These results show that AG2 effectively counters in the convulsant activity of kainic acid. The gradual onset of a lower level of seizure activity after about 90 minutes is commensurate with the reversible action of AG2 observed in brain and heart.

Kainic acid induced seizures have been used as a model for human temporal lobe epilepsy. In addition, abnormal calcium-mediated electrical activity in neurons has been implicated in several types of epilepsy. Therefore, these results indicate that AG2 or its analogues may prove effective in the clinical control of human epilepsy.

EXAMPLE 18

Venom was obtained and isolated from the *Argiope aurantia* spider. The venom used was obtained from Spider Pharm of Black Canyon City, Ariz. The venom was electrically milked from the spiders using a method which employs safeguards to prevent contamination of the venom by abdominal regurgitate and hemolymph.

The first stage in separating the venom was carried out using gel filtration chromatography. Venom was diluted 1 to 10 with phosphate buffered saline and passed over BioGel P-6 using a 0.7×10 cm column eluted with the same buffer Fractions were collected in 1.0 ml aliquots and stored at $-20°$ C.

The protein content of both whole venom and P-6 fractions was determined using conventional methods and measuring absorbance with a Gilford G-2600 spectrophotometer.

Ten microliters of venom that had been diluted 1 to 10 with phosphate buffered saline was mixed with 5 ul of 3× sample buffer. After incubation at 37° C. for 15 minutes 5 ul of each sample was applied to a 10% to 20% gradient polyacrylamide gel using the slab gel method known in the art and the discontinuous buffer system and electrophoresed at 20 watts constant power for 3 hours.

Gels were stained with Coomassie blue staining solution and destained in 10% methanol/10% acetic acid solution. The same procedure was used for electrophoresis of venom fractions except that a 15 ul sample of each fraction was mixed with 7.5 ul of 3× sample buffer and the entire sample was loaded onto the gel. Molecular weights of various fractions were estimated from known standards run on the same gel.

High performance liquid chromatography was performed on the low molecular weight component of the venom using a Vydac C-18 reverse phase column. Components were eluted from the column over a period of 60 minutes using 0% to 60% linear gradient of 60% acetonitrile in 0.1% trifluoroacetic acid. Elution was monitored by absorbance detection at 214 nm. Peaks were collected manually, dried down, and stored at $-20°$ C.

In order to test the effects of the spider venom, late embryos or hatchling chickens were used in all experiments Brain stems were removed and maintained in vitro using methods known and described in the art, except that the temperature in the recording chamber was held at 32° C. The tissue was superfused in avian Tyrode solution at about 1 ml per minute.

The field potential evoked by direct electrical stimulation of the cochlear nerve was recorded with a 4M potassium acetate electrode. The short latency component of the field potential reflects the compound action currents of cochlear nerve axons. This afferent volley is followed by a negativity representing the postsynaptic response of NM neurons.

It was found that *Argiope aurantia* venom blocked synaptic transmission between cochlear nerve axons and their target neurons in the cochlear nucleus (nucleus magnocellularis) without affecting the presynaptic volley. When applied in avian Tyrode solution at a 1 to 300 dilution and a superfusion rate of about 1 ml per minute, whole venom completely blocked the postsynaptic component of the field potential within 15 minutes. Recovery of responses was variable, requiring from 45 minutes to 2 hours. Total blockade with a similar onset and recovery time was seen in a single test of venom diluted 1:600.

Electrophysiological assays of gel-filtration fractions revealed a very clear concentration of activity in the lowest molecular weight fraction. At concentrations equivalent to the 1:300 and 1:600 dilutions of whole venom tested as described above, this gel-filtration fraction caused complete blockade of postsynaptic responses within 15 minutes. Recovery of responses upon washout of this partially-purified toxin occurred from about 45 minutes to 2 hours, as with the whole venom.

Components of this active gel-filtration fraction were further separated using HPLC. Three major peaks and a number of smaller components were seen in the HPLC profile. Electrophysiological assays of the peaks indicated that the largest was the most active. Material in that peak suppressed the postsynaptic response by almost 80% within 5 minutes. The second largest peak also showed some activity, although that component produced only a 40% block. No other components had any significant effect on transmission.

As judged by their migration in Bio-Gel P6, and on SDS-PAGE, the toxic components are of relatively low molecular weight. Material from peaks B and C was examined by fast atom bombardment mass spectrometry. Peak B was a mixture with the two principal components having strong molecular ions (MH$^+$) at m/z 637 and 646. Peak C was also a mixture, the main component giving a strong molecular ion (MH$^+$) at m/z 660 In all cases there were significant peaks corresponding to the doubly-protonated molecular ions at $m/z = (MH_2^{++})/2$, as indicated by half-mass unit spacings.

The ultraviolet absorption spectrum of peak C showed maxima in the near u.v. at 267, 282, and 292 nm, suggesting the presence of a modified aromatic residue. Amino acid analysis after hydrolysis by 6N HCl for 20 hours at 105 C gave Arg and Asp in a ratio of approximately 2:1, plus an unknown compound. High-voltage electrophoresis at pH 6.5 stained positively with ninhydrin and Pauli reagent (specific for His and phenols such as Tyr), but gave no reaction with the Ehrlich stain for Trp. Its mobility relative to peptides of known mass and charge indicated that it carries a net charge of +3 at this pH. Sequential degradation for several cycles in a protein sequencer gave PTH-Arg in the first cycle, but no recognizable derivatives in subsequent cycles.

It was further found that there is no evidence that blockade of transmission in the chick cochlear nucleus is dependent on stimulation frequency. Increasing the rate of cochlear nerve stimulation from 0.2 to 10 Hz during application of toxin caused no obvious increase in the rate of blockade.

In summary, *Argiope Aurantia* toxin was isolated and found to produce a readily reversible blockade of transmission in chick cochlear nucleus.

EXAMPLE 19

Toxin of the *Hololena curta* spider was obtained and purified using the procedure described in Example 4. Using the electrophysiological techniques of Example 16, the toxin so obtained was applied to the chick cochlear nucleus. Assays of all venom fractions obtained by gel-filtration revealed that certain adjacent fractions suppressed synaptic transmission in the chick cochlear nucleus.

The most potent of the gel-filtration fractions, when applied at a dilution of 1:15, completely blocked postsynaptic responses within 10 minutes. Even dilutions of 1:150, if applied to the tissue for longer periods (about 30 minutes) caused a complete blockade of transmission. At no time was there any evidence of recovery of responses for the useful life of the preparation (about 8 hours). The molecular weight of material in the active gel-filtration fractions was 5,000–10,000 daltons as estimated by comparison with known standards run on the same SDS polyacrylamide gels.

These results suggest that this toxin from the *Hoblena curta* spider venom is a patent blocker of transmission in the chick cochlear nucleus mediated by EAA receptors. The results also indicate that the action of the toxin is irreversible or at least very unusually long lasting.

EXAMPLE 20

The high molecular weight toxin described in Example 19 is obtained in the same manner from *Hololena curta* spider venom.

The toxin so obtained is used as a ligand in affinity chromatography to isolate and purify EAA receptors or receptor-channel complexes; the following general procedures are used. Activated polyamide is used as a sorbent-carrier and HO I is used as a ligand. One gram of activated polyamide powder treated by glutaraldehyde is incubated for 24 hours with 11 mg of the toxin in a buffer. The remaining free carrier aldehyde groups are blocked by ethanolamine. Crude synaptosomal preparations from human or animal brain are sonicated. The sonicated membrane fractions are incubated with this affinity sorbent in the presence of NaNO$_2$ for 48 hours. The unbound molecules are carefully washed out and then a pH gradient is used to elute specific molecules bound to the toxin. These molecules are further purified by conventional techniques and their identity as EAA receptors or receptor-channel complexes confirmed by insertion of the molecules into artificial membranes with subsequent pharamcophysiological testing.

EXAMPLE 21

The high molecular weight toxin described in Examples 1-3 (AG1) is obtained in the manner described above from *Agelenopsis aperta* spider venom.

The toxin so obtained is applied for the purpose of labeling calcium channels or receptors in neurons or other cell types. A radioactive label (such as $^3$H, $^{14}$C, or $^{125}$I) is incorporated in the toxin molecule. Binding of the labeled toxin is then assayed using autoradiography of tissue sections or quantifications (using scintillation counting) of binding to various tissue extracts such as synaptosomal or membrane preparations. Autoradiography of brain tissue sections labeled with the radioactive toxin reveals the regional distribution of the calcium channels or receptors to which the toxin binds. (A similar result is obtained by observing the binding pattern of the toxin conjugated to a fluorescent label.) The binding of the toxins to tissue extracts under various conditions, such as the presence of other drugs, provides information regarding the pharmacology of the calcium channel or receptor to which the toxin binds.

EXAMPLE 22

The toxin obtained in the manner described in Example 16 is applied and a complete blockade of synaptic transmission is achieved as described in Example 6. EAA agonists quisqualic and kainic acid are then individually both applied to the cochlear nucleus neurons at concentrations of 5 mM and 50 mM, respectively.

Applications of these agonists at such concentrations normally reduces the ability of cochlear nucleus neurons to respond to direct electrical stimulation, presumably by displaying them by their action on EAA receptors. When applied in the presence of *Argiope aurantia* toxin, however, these agonists have no significant effect; that is, even after 20 minutes of application, these agonists have no effect on the response of cochlear nucleus neurons to direct antidromic stimulation.

The result so obtained indicates that this toxin exerts its effect by acting as an excitatory amino acid receptor antagonist.

EXAMPLE 23

The toxin obtained in the manner described in Example 19 is applied and a complete blockade of synaptic transmission is achieved as described in Example 6. EAA agonists quisqualic and kainic acid are then individually both applied to the cochlear nucleus neurons at concentrations of 5 mM and 50 mM, respectively.

Applications of these agonists at such concentrations normally reduces the ability of cochlear nucleus neurons to respond to direct electrical stimulation, presumably by displaying them by their action on EAA receptors. When applied in the presence of *Hololena curta* toxin, however, these agonists have no significant effect; that is, even after 20 minutes of application, these agonists have no effect on the response of cochlear nucleus neurons to direct antidromic stimulation.

The result so obtained indicates that this toxin exerts its effect by acting as an excitatory amino acid receptor antagonist.

EXAMPLE 24

HO1 isolated as described in Example 19 is used to treat human infections with helminthic worms of the genus Schistosoma. In this example, infection with *S. japohicum* is considered. Treatment with HO1 during acute prmary infection results in clinical improvement of one or more of the following symptoms through reduction in the patient's parasiate load: high spiking fever, chills, cough, urticaria, generalized lymphadenopathy, tender hepatosplenomegaly, eosinophilic leucocytosis, intestinal wall ulcers, abdominal pain, and bloody stools. Treatment with HO1 during later stages of infection reduces one or more of the following symptoms by reduction of the patient's larval load: engorgement of superficial abdominal venous ascites, splenomegaly, anemia, leukopenia, and thrombocytopenia.

IV. SUMMARY

In summary, it can be seen that the methods and compositions of the above invention accomplish the objectives set forth above. In particular, the present invention provides channel blockers or excitatory amino acid receptor blockers which are selectively reversible or irreversible in their effects and which can be used as research tools or in a clinical setting. In particular, the spider toxins of the present invention can be used as channel blockers or excitatory amino acid receptor blockers in the central nervous system, the cardiovascular system, or both systems. In addition, either reversible or irreversible effects can be obtained using the present invention.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A composition functioning as an excitatory amino acid receptor blocker comprising at least one toxin extracted from *Argiope aurantia* spider venom, said at least one toxin being capable of functioning as an excitatory amino acid receptor blocker.

2. A composition as defined in claim 1 wherein the effects of the toxin are reversible.

3. A composition as defined in claim 1 wherein the effects of the toxin are irreversible.

4. A composition as defined in claim 1 wherein the toxin blocks excitatory amino acid receptors in the nervous system.

5. A composition as defined in claim 1 wherein the toxin has a molecular weight of from about 500 to about 1,000 daltons.

6. A composition as defined in claim 5 wherein the effects of said toxin are reversible.

7. A composition functioning as an excitatory amino acid receptor blocker comprising a toxin extracted from the venom of the *Argiope aurantia* spider and having a molecular weight of from about 500 to about 1,000 daltons.

8. A composition as defined in claim 7 wherein the toxin has a molecular weight of from about 650 to about 670 daltons.

9. A composition as defined in claim 8 which produces a readily reversible blockage of transmission in chick cochlear nucleus.

10. An insecticide consisting essentially of at least one toxin extracted from the whole venom of the *Agelenopsis aperta* spider.

11. An insecticide as defined in claim 10 wherein the toxin has a molecular weight of from about 500 to about 1,500 daltons.

12. An insecticide as defined in claim 10 wherein the toxin has a molecular weight of from about 5,000 to about 10,000 daltons.

13. An insecticide comprising a toxin extracted from the whole venom of the *Hololena curta* spider and having a molecular weight of from about 5,000 to about 7,000 daltons.

14. An insecticide functioning as an excitatory amino acid receptor blocker comprising a toxin extracted from the *Argiope aurantia* spider and having a molecular weight of from about 500 to about 1,000 daltons.

15. An anthelmintic functioning as an excitatory amino acid receptor blocker comprising a toxin extracted form the *Argiope aurantia* spider and having a molecular weight of from about 600 to about 700 daltons.

16. A composition as defined in claim 1 wherein said toxin has a molecular weight of approximately 660 daltons.

17. A composition as defined in claim 16 wherein the effects of said toxin are reversible.

18. A method of manufacturing an excitatory amino acid receptor blocker comprising the steps of:

(a) obtaining at least one *Argiope aurantia* spider;

(b) obtaining venom from said at least one spider;

(c) separating the toxins of the venom so obtained;
(d) recovering an individual toxin separated from the venom; and
(e) combining said isolated toxin with a pharmaceutically acceptable carrier such that the toxin is capable of functioning as an excitatory amino acid receptor blocker.

19. A method as defined in claim 18 wherein the toxin recovered has a molecular weight of from about 500 to about 1,000 daltons.

20. A method of administering an excitatory amino acid receptor blocker comprising the steps of:
(a) obtaining an excitatory amino acid receptor blocker composition comprising at least one toxin isolated from the venom of the *Argiope aurantia* spider, said isolated toxin being combined with a pharmaceutically acceptable carrier such that the composition is capable of functioning as an excitatory amino acid receptor blocker; and
(b) administering said excitatory amino acid receptor blocker composition to a human patient.

21. A method of administering an excitatory amino acid receptor blocker as defined in claim 20 wherein the at least one toxin isolated from the venom of the *Argiope aurantia* spider has a molecular weight of from about 500 to about 1,000 daltons.

* * * * *

UNITED STATES PATENT AND TRADEMARK OFFICE
CERTIFICATE OF CORRECTION

PATENT NO. : 5,064,657

DATED : November 12, 1991

INVENTOR(S) : J. R. HUNTER JACKSON et al.

It is certified that error appears in the above-identified patent and that said Letters Patent is hereby corrected as shown below:

Column 1, line 6, insert the following paragraph:

--This invention was made with government support under grant #NIH NS 17257 and grant #NIH NS 15132 awarded by the National Institute of Health. The government has certain rights in the invention.--

Column 2, line 3, "neurotransmitter" should be --neurotransmitters--
Column 4, line 11, "Thus," should be --This--
Column 7, line 42, after "cell" insert --.--
Column 8, line 63, delete "than"
Column 9, line 59, after "nucleus" insert --.--
Column 10, line 53, "features" should be --feature--
Column 13, line 1, after "transmitter" insert --.--
Column 14, line 52, "abou" should be --about--
Column 15, line 16, "on heart" should be --on the heart--
Column 15, line 28, "in heart" should be --in the heart--
Column 15, line 53, after the second ";" insert --and--
Column 16, line 36, "symptions" should be --symptoms--
Column 17, line 14, "qr" should be --or--
Column 17, line 30, "achute" should be --acute--
Column 18, line 16, after "buffer" insert --.--

UNITED STATES PATENT AND TRADEMARK OFFICE
CERTIFICATE OF CORRECTION

PATENT NO.   :   5,064,657
DATED        :   November 12, 1991
INVENTOR(S)  :   J. R. HUNTER JACKSON et al.

It is certified that error appears in the above-identified patent and that said Letters Patent is hereby corrected as shown below:

```
Column 18, lines 48-49, after "experiments" insert --.--
Column 21, line 41, "prmary" should be --primary--
Column 21, line 43, "parasiate" should be --parasite--
Column 22, line 57, "form" should be --from--
```

Signed and Sealed this

Twenty-sixth Day of October, 1993

Attest:

BRUCE LEHMAN

*Attesting Officer*           *Commissioner of Patents and Trademarks*